United States Patent [19]
Kopelowicz

[11] 3,951,141
[45] Apr. 20, 1976

[54] PRESERVATIVE OF ELASTIC MATERIAL

[76] Inventor: Alberto Kopelowicz, Helguera 4556, Buenos Aires, Argentina

[22] Filed: Dec. 19, 1974

[21] Appl. No.: 534,345

[30] Foreign Application Priority Data
May 7, 1974  Argentina ............................ 253622

[52] U.S. Cl. ................................................ 128/294
[51] Int. Cl.² .......................................... A61F 5/42
[58] Field of Search ................ 128/132 R, 294, 79; 206/69

[56] References Cited
UNITED STATES PATENTS
2,448,938  9/1948  Wayne ................................ 128/294
3,677,225  7/1972  Czirely ............................ 128/132 R FOREIGN PATENTS OR APPLICATIONS
420,932  12/1910  France ................................ 128/294

Primary Examiner—Lawrence W. Trapp
Attorney, Agent, or Firm—Wenderoth, Lind & Ponack

[57] ABSTRACT

A contraceptive device formed of elastic material includes an extensible cap-shaped element having folds in the form of a bellows. The integral base of the element extends outwardly in the form of a planar annular flange having attached to the outer border thereof a rigid ring. The area of juncture between the cap and flange is defined by a plurality of apertures or perforations, whereby slight pressure exerted on the ring allows separation of the flange from the cap. The lower edge of the interior of the cap has applied thereto an adhesive band for adhering the cap to the glans of a male organ.

4 Claims, 4 Drawing Figures

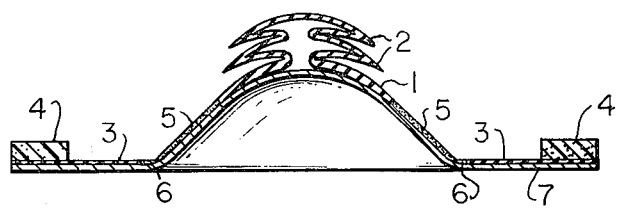
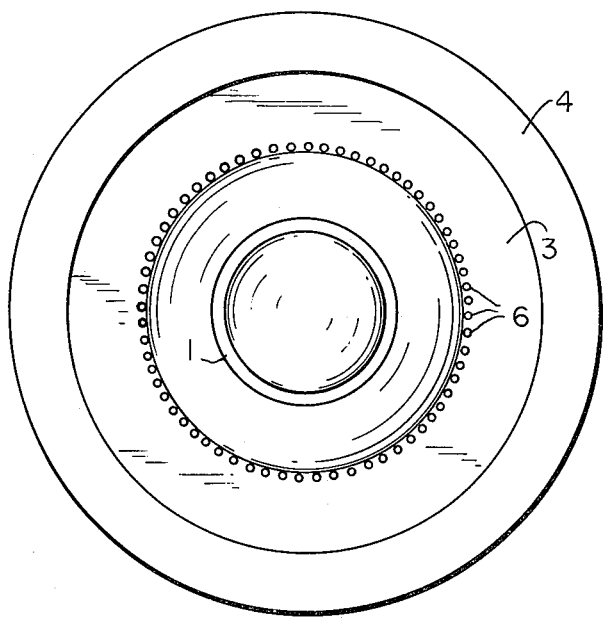
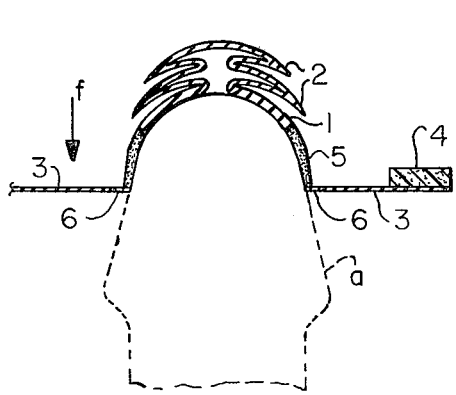
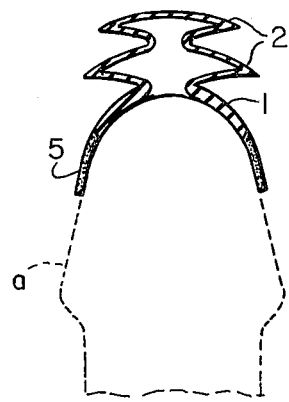

PRESERVATIVE OF ELASTIC MATERIAL

BACKGROUND OF THE INVENTION

The present invention relates to an improved contraceptive and protective device of the type in the form of a cap for covering the top or outermost zone of the glans of a male organ. More particularly, the present invention relates to such a device provided with means for the easy and convenient placement thereof.

Cap-type contraceptive devices intended to cover only the glans of a male organ are known. However, such devices are difficult to put in place and are normally uncomfortable.

SUMMARY OF THE INVENTION

With the above discussion in mind, it is the object of the present invention to provide a cap-type contraceptive device of flexible material and extensible form which fits the glans of a male organ and which includes an integral disk for facilitating placement of the device, the disk being readily removable when the device is in place.

According to the invention, the contraceptive device is in the form of a cap-shaped element having an extensible bellows. The base of the cap extends outwardly in the form of a planar annular flange which has attached to the outer border thereof a rigid annular ring. The area of juncture of the cap and base is defined by a plurality of perforations. The integral lower edge of the cap is covered by a band of adhesive material for fixing the cap to the glans of a male organ. Once the cap is in position, the ring is grasped, and with a slight force applied thereto, the flange is separated from the cap along the perforations.

Before use, the interior or lower surface of the entire device is covered by a protective sheet of cloth or similar material.

BRIEF DESCRIPTION OF THE DRAWINGS

To attain a clear understanding of the present invention and the manner of use thereof, reference will be made to the following detailed description, taken with the attached drawings, in which:

FIG. 1 is a section of both the contraceptive device and the integral supporting disk thereof, prior to use;

FIG. 2 is a plan view of the device of FIG. 1;

FIG. 3 is a section of the device, with the protective covering thereof removed, and at the moment the device is put in place; and FIG. 4 is a section of the device, similar to FIG. 3, but with the supporting disk removed.

DETAILED DESCRIPTION OF THE INVENTION

In the figures similar reference numerals indicate similar elements.

With reference to the drawings, the contraceptive device of the invention includes a cap-type element 1 formed of elastic material. Element 1 is provided at the outer end thereof with annular folds in the form of a bellows, such that element 1 is extensible. Integral with element 1 is a base in the form of an outwardly extending annular flange 3. The outer border of flange 3 has fixed thereto a rigid annular ring 4.

Internally along the lower edge of the element there is provided a band of adhesive material 5, intended for fixing the contraceptive device to the glans of a male organ. In the area of the device where flange 3 adjoins element 1, there are provided a plurality of perforations 6, which permit easy separation, upon the application of a slight force, of the flange 3 from the cap element 1.

To protect the contraceptive device and adhesive band 5, the interior or lower part of the entire device is covered with a protective cloth, tissue or similar material 7, which is slightly but removably adhered thereto.

When the contraceptive device is to be used, the protective cloth 7 is removed, and the entire device is grasped by the annular ring 4, and positioned in place with cap element 1 on the top or end of glans $a$, as is illustrated in FIG. 3, the configuration of element 1 being dome-shaped to closely fit glans. Adhesive band 5 adheres to the glans. Thereafter, a slight force, applied in the direction indicated by arrow $f$, on ring 4 will cause ring 4 and flange 3 to be separated from cap element 1 along the ring of perforations 6. The element 1 will then be in operative position as illustrated in FIG. 4.

Due to the provision of relatively rigid ring 4 and annular flange 3, the contraceptive device may easily be placed and fixed in position without the need of contact with either adhesive band 5 or element 1.

Various modifications may be made to the specific structural arrangement described above without departing from the scope of the invention.

I claim:

1. A contraceptive and sanitary protective device comprising:
   a cap element formed of elastic material and having an open end and a closed end;
   said closed end having annular folds forming a bellows;
   said cap element having on the interior thereof, adjacent said open end, a band of adhesive material for adhering said cap element to the glans of a male organ;
   said cap element having integral therewith, at said open end thereof, a planar base in the form of an annular flange extending outwardly from said cap element;
   the area of juncture between said open end of said cap element and said flange having therein a plurality of perforations; and
   ring means, formed or rigid material and attached to said flange, for separating said flange from said cap element along said perforations after said cap element is adhered in place.

2. A device as claimed in claim 1, wherein said perforations are closely spaced in a ring-shaped formation.

3. A device as claimed in claim 1, further comprising a protective cloth removably adhered to the interior of said cap element and the lower surface of said flange.

4. The device claimed in claim 1, wherein said ring means is attached to said flange adjacent to the outer annular border thereof.

* * * * *